US005628407A

United States Patent [19]
Gilbert et al.

[11] Patent Number: 5,628,407
[45] Date of Patent: May 13, 1997

[54] METHOD AND APPARATUS FOR SEPARATION OF MAGNETICALLY RESPONSIVE SPHERES

[75] Inventors: Douglas C. Gilbert, Ledyard; Peter G. Cable, Old Lyme, both of Conn.

[73] Assignee: Bolt Beranek and Newman, Inc., Cambridge, Mass.

[21] Appl. No.: 349,627

[22] Filed: Dec. 5, 1994

[51] Int. Cl.$^6$ .................... B03C 1/00; B01D 35/06
[52] U.S. Cl. .............. 209/214; 209/223.1; 209/227; 209/232; 210/222; 210/695; 422/101; 436/177
[58] Field of Search ................... 209/214, 223.1, 209/224, 225, 226, 227, 228, 231, 232; 210/222, 223, 695; 422/67, 101; 436/177

[56] References Cited

U.S. PATENT DOCUMENTS

| | | | |
|---|---|---|---|
| 3,582,017 | 6/1971 | Zecca . | |
| 3,951,784 | 4/1976 | Kaiser et al. | 209/1 |
| 4,663,029 | 5/1987 | Kelland et al. | 209/232 X |
| 4,778,594 | 10/1988 | Doctor | 209/224 |
| 4,784,759 | 11/1988 | Elliott | 209/224 X |
| 4,910,148 | 3/1990 | Sorensen et al. | 209/213 X |
| 4,941,969 | 7/1990 | Schonert et al. | 209/232 X |
| 4,988,618 | 1/1991 | Li et al. | 435/6 |
| 5,045,189 | 9/1991 | Van der Vos et al. | 210/223 X |
| 5,147,529 | 9/1992 | Lee et al. | 436/177 X |
| 5,158,871 | 10/1992 | Rossomando et al. | 435/7.32 |
| 5,169,006 | 12/1992 | Stelzer | 209/232 X |
| 5,183,638 | 2/1993 | Wakatake | 210/222 |
| 5,186,827 | 2/1993 | Liberti et al. | 422/64 |
| 5,200,084 | 4/1993 | Liberti et al. | 210/222 X |
| 5,238,577 | 8/1993 | Newsom | 210/222 |
| 5,279,936 | 1/1994 | Vorpahl | 435/6 |
| 5,356,713 | 10/1994 | Charmot et al. | 428/407 |

*Primary Examiner*—William E. Terrell
*Assistant Examiner*—Tuan Nguyen
*Attorney, Agent, or Firm*—Brian L. Michaelis

[57] ABSTRACT

A method and apparatus for automated separation of fluid borne magnetically responsive spheres into different populations by carefully manipulating forces of gravity, buoyancy, fluid friction, and magnetism. Distinct homogeneous sphere populations are separated from a non-homogeneous population including a plurality of intermixed homogeneous sphere populations, without significant manual processing, by: effecting magnetic distancing of an initial non-homogeneous sphere population; facilitating enhanced separation of the non-homogeneous population in accordance with rate of descent of spheres within homogeneous populations; providing magnetic acceleration of the separation process; and effecting magnetic concentration of the separated homogeneous sphere populations. The process and apparatus provide for improved bio-sensing resulting from the automated condensing of homogeneous groups of spheres from a non-homogeneous sphere population.

17 Claims, 4 Drawing Sheets

DESCENT SPEED OF PATHOGENS AFFIXED TO BEADS

UNATTACHED BEAD RATE OF
DESCENT IN WATER:

500 μm/MIN (5.0 μm BEADS)
100 μm/MIN (2.5 μm BEADS)

4 = N° ATTACHED BEADS

DESCENT SPEED OF PATHOGENS AFFIXED TO BEADS

PATHOGEN RADIUS ÷ BEAD RADIUS

FIG. 2

METHOD AND APPARATUS FOR SEPARATION OF MAGNETICALLY RESPONSIVE SPHERES

FIELD OF THE INVENTION

The present invention relates to magnetic separation, and more particularly to the magnetic separation of magnetically responsive spheres admixed in a fluid.

BACKGROUND OF THE INVENTION

A common method for identifying the presence of organic or inorganic substances in fluids involves capturing the substances with specially treated magnetically responsive spheres that are designed to attach themselves to a substance of interest. The nature of the spheres allows for magnetic management of the spheres in that such spheres are highly permeable with low magnetic retentivity. Thus, the spheres are responsive to and can be manipulated by magnetic fields, yet when the magnetic fields are removed the particles retain no magnetic properties.

Such spheres, or magnetically responsive particles, are commercially available, among other sources, from Dynal Inc., 45 North Station Plaza, Great Neck, N.Y., in 2.8 and 4.5 micron diameter sizes (hereinafter referred to as "Dynal beads" or "beads"). Dynal beads have been used as magnetically responsive beads for isolating, collecting and assaying diagnostic ligates as described in U.S. Pat. No. 5,158,871 ("the '871 patent").

As disclosed in the '871 patent, a suitable ligand is bound to a sheath of an organic substance surrounding the metal oxide core of the magnetically responsive beads. The suitable ligand is capable of binding with a ligate or target substance that is sought to be isolated and is diagnostic of a particular disease state. The ligand/beads are admixed with a fluid containing the ligate sought, for a selected time period and in a manner sufficient to effect a strong attachment between the ligate and ligand/beads to form ligate/ligand/bead complexes.

A magnetic gathering or harvesting device is contemplated in the '871 patent, to attract and retain the complexes in a localized magnetic field for removal from the fluid. The '871 patent suggests only application specific, manually manipulated harvesting devices each suitable for a particular application.

Other known procedures for magnetically managing such beads or other magnetically responsive spheres, typically involve insertion of the magnetically responsive spheres into a fluid to be tested after the spheres have been treated with the appropriate bonding agent for the test. The spheres are admixed in the fluid by shaking, stirring, or pumping to allow for the spheres to come into contact with the target substance. After the complexing phase is complete, i.e., the target substance has been sufficiently exposed to the magnetically responsive spheres with associated bonding agent within the fluid to form sphere/bonding agent/target substance complexes, the complexes including the spheres are removed from the fluid by attracting them toward a particular location with a magnet. Typically, bead concentration is much greater than target substance concentration. Thus, a large number of beads remain free of target substance and some portion of the bead population is bound with target substance.

The non-homogeneous population of target substance bound and unbound spheres is drawn in bulk toward and concentrated in the vicinity of a controller magnet. Manual processing for the separation of the spheres can take many hours and is labor intensive. Only after considerable manual processing can spheres be separated from different populations for microscopic slide preparation. The spheres can then be tested to determine the presence of target substances attached to the surfaces of the spheres. To enhance the capture process, large numbers of spheres are often used. In addition, spheres of different sizes, each treated for a different target substance, may be used. In these cases, it is necessary and desirable, yet difficult, time consuming, labor intensive and costly, to separate spheres from different populations into homogeneous populations for further analysis.

SUMMARY OF THE INVENTION

The present invention provides a method and apparatus for automated separation of magnetically responsive spheres into different populations by carefully manipulating forces of gravity, buoyancy, fluid friction, and magnetism. According to the invention, distinctly homogeneous sphere populations are separated from a non-homogeneous population comprised of a plurality of intermixed homogeneous sphere populations, without significant manual processing, by: magnetically effecting distancing of an initial non-homogeneous sphere population; facilitating enhanced separation of the non-homogeneous population in accordance with rate of descent of spheres within homogeneous populations; providing magnetic acceleration of the separation process; and effecting magnetic concentration of the separated homogeneous sphere populations.

Features of the process and apparatus according to the invention include benefits obtained in the art of bio-sensing resulting from the automated condensing of homogeneous groups of spheres from a non-homogeneous sphere population. Such benefits include improved detection, classification and quantitation of target substances. Laboratory test times are reduced due to the elimination of the requirement to test all sphere populations. Sampling efficiency is improved due to the ability to test for multiple target substances using spheres of different sizes. The testing process can be more fully automated by counting the separated spheres with magnetic or imaging techniques.

The method and apparatus can be implemented as a laboratory test device, an automated laboratory system, a portable field unit, or an in-line continuous real-time monitor. Further features include: exceptionally high separation efficiency and exceptionally rapid separation to facilitate exceptionally rapid examination. Additionally, unbound beads effectively separated can be recycled/reused.

BRIEF DESCRIPTION OF THE DRAWINGS

Other features and advantages of the invention will be apparent from the following detailed description of an illustrative embodiment, read in conjunction with the accompanying drawings in which:

FIG. 2 is a graph illustrating calculated relative rates of descent of illustrative bead bound pathogens in an illustrative fluid.

DETAILED DESCRIPTION

Figure 1A:
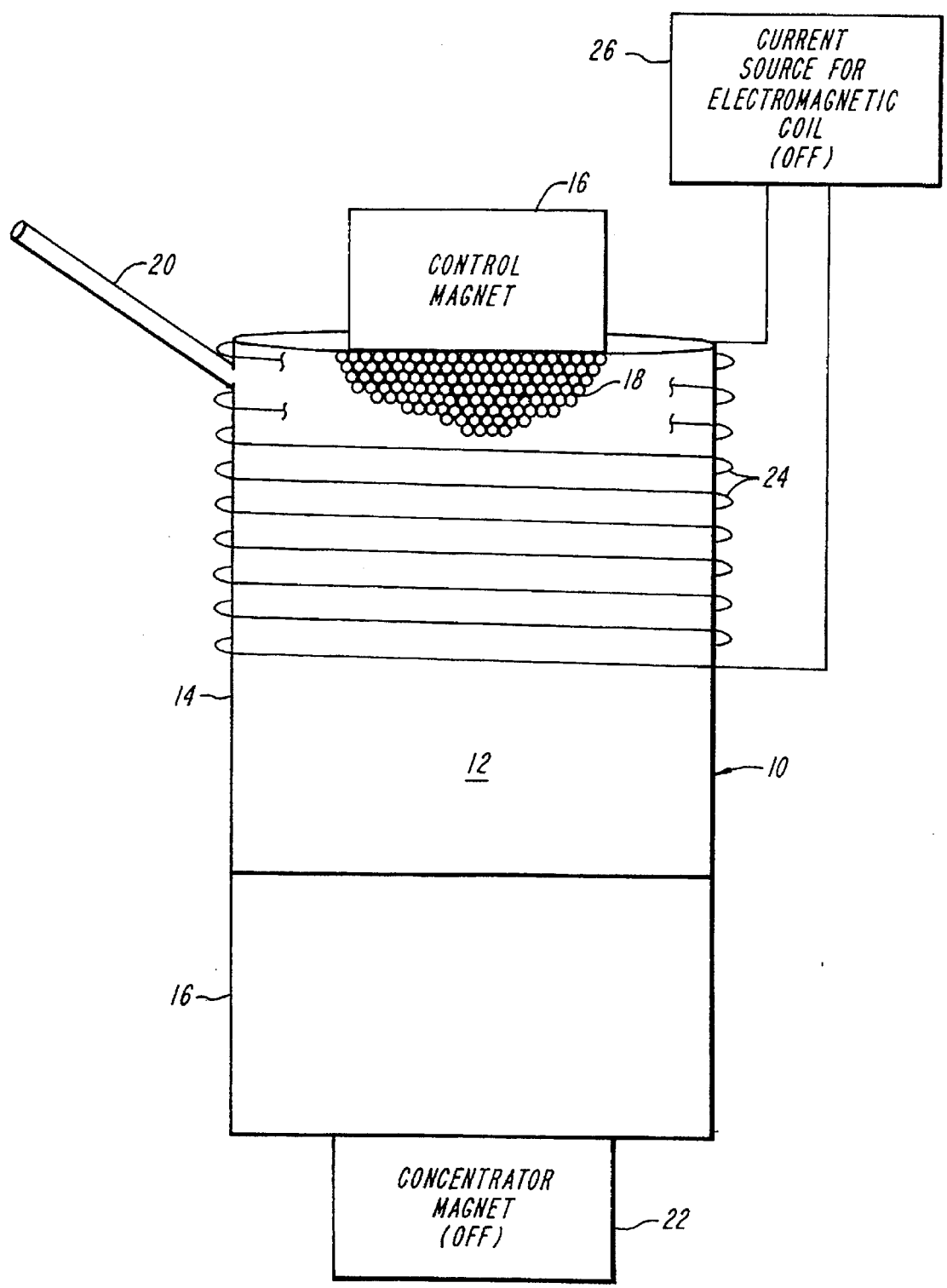
FIG. 1A is a diagrammatic representation of an apparatus for containing a fluid with a target substance and magnetically responsive beads for implementing the method of separating the magnetically responsive beads according to the invention.
Figure 1B:
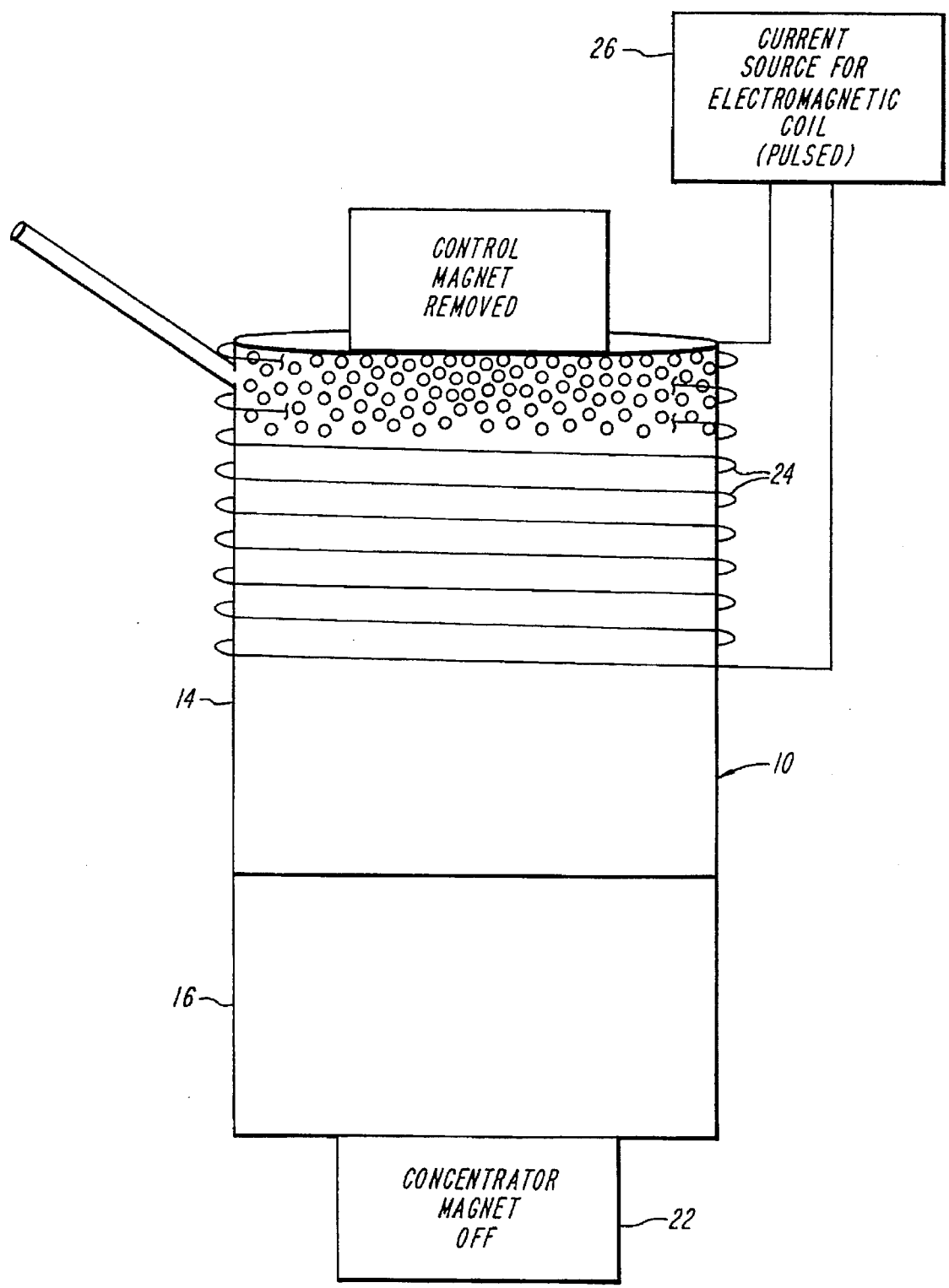
FIG. 1B is the apparatus of FIG. 1A wherein a disbursed bead cloud is formed.

Referring now to FIG. 1A, an illustrative apparatus for performing the method of separating magnetically responsive beads according to the invention generally includes a cylinder or column 10 which contains a fluid 12. The column 10 has a substantially vertical orientation so as to define a top portion 14 and a bottom portion 16 thereof. The top portion 14 includes a control magnet 17 that facilitates control of a non-homogeneous mixture of magnetically responsive beads 18 when it is desirable to retain the beads 18 at the top portion 14 of the column 10. The control magnet can be a permanent magnet or an electromagnet, so long as its magnetic properties can be removed as discussed hereinafter. The top portion 14 also includes a duct or port 20 for introducing the beads 18 and/or fluid 12 into the column.

The bottom portion 16 of the column 10 is preferably separable from the top portion 14 to facilitate removal of captured particles. Separability also permits easy access and cleaning of the interior of the column 10. A concentrator magnet 22 is disposed proximate to the bottom portion 16 for expediting descent of beads within the column as discussed hereinafter.

A plurality of turns 24 of an electrically conductive wire coil are wound around the column 10 constituting an electromagnetic field generator that further includes a current source 26. The current source 26 selectively delivers current to the coil turns 24 to provide an initial magnetic pulse and to set up electromagnetic lines of flux in a direction substantially parallel to a direction of descent of beads within the column. In this illustrative embodiment, the electromagnetic coil turns 24 are wound around the top portion 14 of the column 10 so as not to interfere with the separability of the top and bottom portions of the column. However, it will be appreciated that the relative dimensions of the column top and bottom portions may differ from the present illustrative embodiment and the coil turns may extend to part of the bottom portion or be entirely disposed thereon. It should be appreciated as well, that the electromagnetic coil can be implemented in a Helmholtz configuration, having an appropriate gap between coil portions to facilitate visual or other observation, and simplify implementation of the process while providing a constant magnetic field.

A large quantity of the magnetically responsive beads or spheres, having a suitable outer sheath of bonding agent for binding with a target substance, are admixed in a fluid for a sufficient time and in a sufficient manner to allow for the spheres to come into contact with the target substance. It should be appreciated that such admixing can be done in the column 10, or in a container other than the column whereupon the beads or complexes would be collected, transported and injected into the column for the separation process. Once the complexing phase is complete, i.e., the target substance has been sufficiently exposed to the magnetically responsive spheres with associated bonding agent within the fluid to form sphere/bonding agent/target substance complexes, it is desirable to effect control of the magnetically responsive spheres for commencement of the separation process.

In an initial condition, as illustrated in FIG. 1A, the magnetically responsive spheres are disposed within the fluid 12 in the column 10 and retained against a horizontal surface via the control magnet 17 until the separation process begins. As the spheres are all clustered in the vicinity of the magnet, there is a tendency for the spheres to adhere to each other due to non-magnetic forces of compression and surface tension. This is especially true of spheres with diameters of a few microns. Despite the fact that the spheres are "magnetically responsive" and exhibit minimal magnetic retentivity, if any, there is a tendency for the spheres to adhere to one another even after removal of the control magnet. Thus, it is necessary to excite the beads in order to eliminate clustering. The very small nature of the beads and the viscosity of the fluid creates a situation wherein large amounts of turbulence in the column, as would be created by stirring, shaking or the like, prolongs agitation of the beads and slows the separation process. It is preferable to create a localized agitation without creating great amounts of turbulence so that the viscous forces of the fluid in motion are not so dominant as to slow or impede the separation process.

As illustrated in FIG. 1B, by simultaneously removing the control magnet and applying a magnetic field impulse with sufficient flux to drive the magnetically responsive beads into magnetic saturation, the spheres will move to form chains that align with the flux lines of the applied field. The chains will maintain cross-field separation due to the repelling forces of like dipoles. The magnetic field impulse, the magnitude of which is a function of the composition, size and quantity of beads, is applied only long enough to generate motion within the spheres, and then released. The magnitude of the magnetic field impulse is controlled by the diameter and number of turns of the coil, and the current therethrough. The sphere motion and resultant localized fluid motion generated by the field impulse will eliminate the clusters, effecting an initial separation and creating a cloud of beads at the top portion of the column. The initial electromagnetic impulse, in conjunction with removal of the control magnet, excites each of the spheres into separate free-fall descent paths. Note that this concept may be applied to negatively buoyant spheres that fall through a fluid column, or to positively buoyant spheres that rise through a fluid column, or to combinations of positively and negatively buoyant spheres within a fluid column.

Further separation of the spheres is a function of the relative rates of descent (or ascent) of the beads or spheres. Free falling (or free rising) spheres in the fluid reach terminal velocity which can be computed as a function of sphere mass, sphere diameter and roughness, and fluid density and viscosity. With no magnetic forces (other than gravitational forces) acting on the beads, as illustrated in FIG. 1C, the beads begin to fall as a distributed cloud and aggregate into homogeneous populations in accordance with common characteristics and rate of descent or motion within the particular fluid. A free-fall period of time is required to allow for vertical separation of homogeneous groups. Vertical separation is a function of descent rate. The nature of the homogeneous groups is such that spheres within each group will have a common descent rate, while different homogeneous groups have different descent rates. Many target substances may exhibit neutral buoyancy in the fluid in the column and act to slow the rate of descent of the attached bead, thus facilitating separation.

FIG. 2 shows a set of curves that describe the descent rates of bead-bound pathogens in water as a function of sphere mass and roughness and fluid density and viscosity calculations. The microbeads are typically 2.8, 4.5, or 10.0 microns in diameter as discussed hereinbefore, and when a bead comes in contact with the pathogen or target substance the bead attaches to the organism. As the negatively buoyant magnetically responsive beads descend at rates that relate to their particular condition, the populations will separate according to descent rates. As is illustrated in FIG. 2, the descent rates of micro spheres can be very slow (100 to 500 microns per second), so it is desirable to accelerate the process.

Figure 1C:
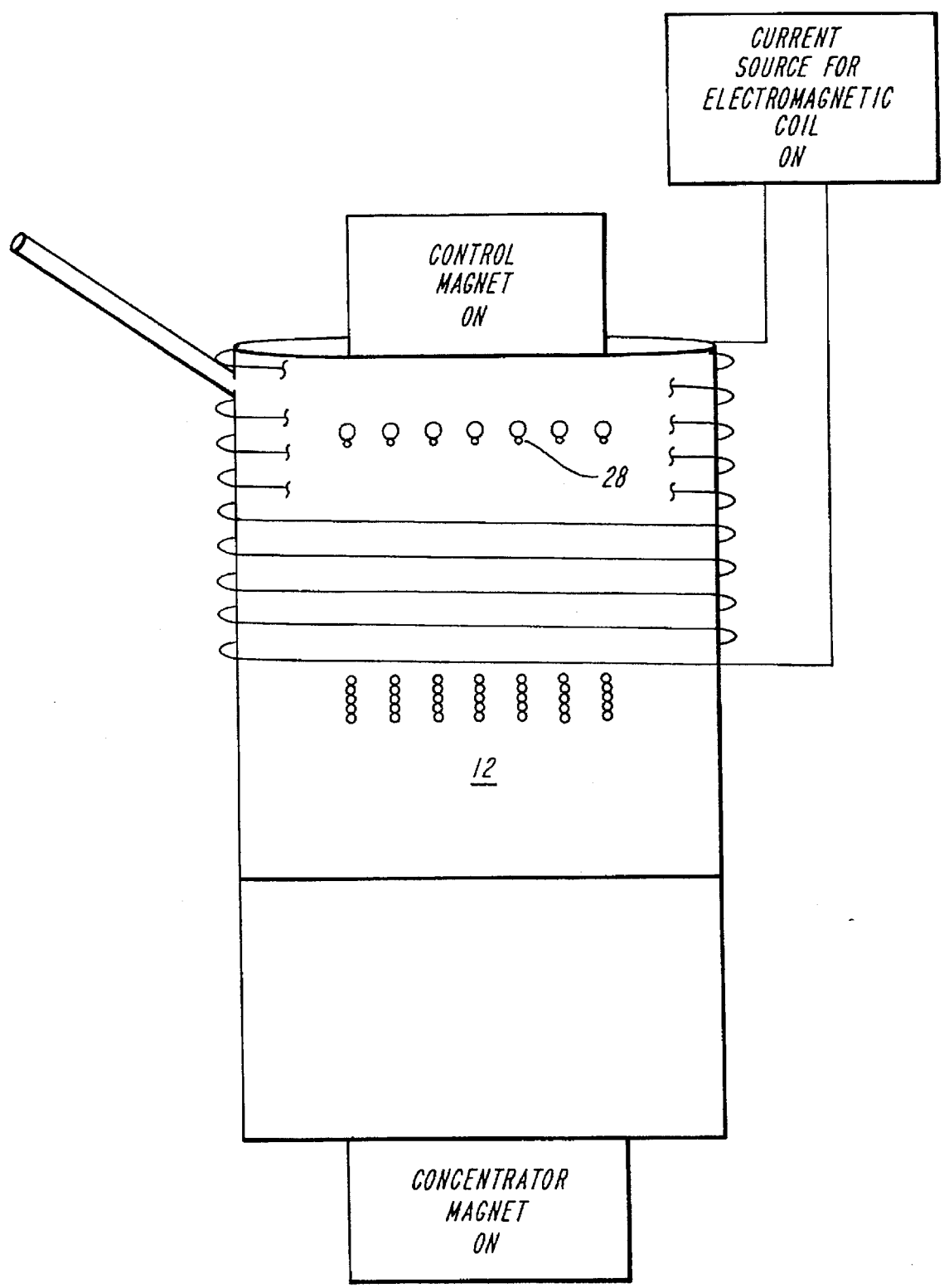
FIG. 1C is the apparatus of FIG. 1A wherein the magnetically responsive beads are subject to separation in accordance with relative rates of descent.

The separation process according to the invention is enhanced by magnetic acceleration. Once the sphere populations have achieved separation distances on the order of a few diameters, a vertical and constant magnetic field can be applied to the fluid column. As illustrated in FIG. 1C, the spheres in each of the separated populations will chain up in vertical orientation. A general observation regarding the present illustrative embodiment, is that beads that are not attached to a target substance aggregate as dipole "spears" which tend to descend faster than bead/target substance aggregates 28. In this orientation, the rates of descent will be magnified by the number of spheres in each chain, amplifying the separation process. Application of a permanent magnet at the bottom of the fluid container will further amplify the separation speed because the spheres closest to the magnet will be drawn with the strongest magnetic force.

Once the sphere populations have reached sufficient separation distances in the illustrative embodiment, a second permanent magnet with equal magnetic force relative to the first magnet will be placed at the top of the fluid container. The magnetic force of the bottom magnet will draw the fastest descent spheres to the bottom of the fluid column, and the magnetic force of the top magnet will draw the slowest descent beads to the top of the fluid column. The separation process can be completed in a matter of minutes. A primary determinant of the time required is the length of the column, which is preferably as short as practicable so as to expedite the process. Upon completion of the separation the upper and lower magnets control the separated populations. The fluid can be drawn off from the column and the upper and lower portions of the column separated to provide access to the populations for further preparation and testing.

In order to separate pathogens or target substances that are particularly small, and therefore do not act to buoy or slow the descent of a bead to which they attach, it may be desirable to attach a larger, non-magnetically responsive bead to the bead/target substance combination. Neutrally buoyant, non-magnetically responsive beads are available that can be sheathed to bind to a different binding site on the target substance than the sheath on the magnetically responsive bead. Accordingly, a bead can be selected to combine with the magnetically responsive bead/target substance complex so as to effect a desired rate of descent and assure a high degree of homogeneous grouping in the descending beads. In such a case, the separation, acceleration and concentration aspects of the process according to the invention are not substantially changed.

Although a single coil with a plurality of turns is implemented in the illustrative embodiment shown and described herein to provide both the initial magnetic impulse and the vertically oriented magnetic field, it should be appreciated that different magnetic mechanisms can be implemented to effect both the initial magnetic impulse and the vertically oriented magnetic field. For instance, a vertically or horizontally oriented electromagnet could be used to effect the electromagnetic impulse. Or a combination of vertical and horizontal with alternating electromagnetic impulses could be used for initial separation. Similarly, a separate Helmholtz coil or other magnetic mechanism could be used to effect the vertically oriented magnetic field for separation acceleration.

Furthermore, it should be appreciated that magnetic concentration can be effected at the sides, as opposed to the top of the column, and such concentration may be effected on a plurality of populations using a plurality of concentrator magnets in excess of two.

While the invention is described herein as involving a "fluid" generally, it should be appreciated that respective ones of numerous fluids can be implemented having differing viscosities and fluid properties, with differing affects on the separation process according to the invention. For instance, alternative fluids, such as various forms of impure water may be implemented, or other liquids, or gases, or the like.

Likewise, while the illustrative embodiment described hereinbefore includes the use of very small beads, it should be appreciated that larger beads may be involved, and that bead sizes can be specified according to particular separation applications. Furthermore, although "magnetically responsive", commonly known as "paramagnetic", beads are used in the illustrative embodiment described herein, it should be appreciated that other generically described beads that are susceptible to magnetic manipulation can be implemented such as magnetically soft spheres or the like.

Although the illustrative embodiment described hereinbefore includes a column or vertically oriented cylindrical container 10 containing the fluid 12 and magnetically responsive beads, it will be appreciated by those of ordinary skill in the art that other vessels and orientations may be used in implementing the apparatus and method according to the invention, and that such vessels need not be cylindrical in shape.

While the column 10 as illustrated includes a single port or duct 20 for introducing beads and/or a fluid into the column, it will be appreciated that other means for introducing things into the vessel can be implemented, such as a plurality of ducts or ports, or hoses, spouts, conduits or the like.

Similarly, while the column is separable, it should be appreciated that alternative mechanisms may be implemented for removing the concentrated beads from the column, such as ports or ducts in the bottom or other portion for the purpose of the drawing the concentrated beads out of the column or vessel.

Although the invention has been shown and described with respect to an illustrative embodiment thereof, various other changes, omissions and additions in the form and detail thereof may be made therein without departing from the spirit and scope of the invention.

What is claimed is:

1. A method of separating at least one homogeneous population of magnetically responsive bead aggregations from a non-homogeneous population of magnetically responsive beads including said at least one homogeneous population of magnetically responsive bead aggregations and other magnetically responsive beads admixed in a fluid in a container having a first portion and a second portion, said method comprising the steps of:

controlling said non-homogeneous population of magnetically responsive beads admixed in said fluid using a control magnetic field to retain said non-homogeneous population of magnetically responsive beads in said first portion of said container;

removing said control magnetic field;

generating an electromagnetic impulse to excite and de-cluster said non-homogeneous population of magnetically responsive beads admixed in said fluid to effect an initial separation of said non-homogeneous population of magnetically responsive beads and to effect a first rate of motion of said non-homogeneous population of magnetically responsive beads in a first direction away from said first portion of said container and toward said second portion of said container;

applying a magnetic field to said non-homogeneous population of magnetically responsive beads to effect a second rate of motion of said other magnetically responsive beads and a third rate of motion of said at least one homogeneous population of magnetically responsive bead aggregations; and concentrating said at least one homogeneous population of magnetically responsive bead aggregations at at least a first concentrator magnet.

2. The method of claim 1 further including the step of concentrating said other magnetically responsive beads at at least one second concentrator magnet.

3. The method of claim 1 wherein said container is a substantially vertical column and said first portion is a top of said column and said second portion is a bottom of said column.

4. The method of claim 1 wherein said step of removing and said step of generating are performed substantially simultaneously.

5. The method of claim 3 wherein said first concentrator magnet is located proximate to said top of said column.

6. The method of claim 2 wherein said at least one second concentrator magnet is located proximate to a bottom of said container.

7. An apparatus for performing the method of claim 1.

8. The method of claim 1 wherein said step of applying a magnetic field involves applying said magnetic field co-linear with said first direction.

9. An apparatus for separating a first population of magnetically responsive particles from a second population of magnetically responsive particles in a fluid, said second population of magnetically responsive particles including said first population of magnetically responsive particles and a third population of at least some other magnetically responsive particles, comprising:

a container having a first portion and a second portion, said container receiving and containing said fluid and including said first population of magnetically responsive particles and said third population of at least some other magnetically responsive particles;

a control magnet proximate to said first portion of said container, said control magnet effecting a removable control magnetic field to retain said second population of magnetically responsive particles in said first portion of said container;

a controllable magnetic field proximate to said container, said controllable magnetic field being controllable to deliver at least one of a magnetic impulse and a magnetic field to said second population of magnetically responsive particles; and at least one concentrator magnet disposed proximate to said second portion of said container, said at least one concentrator magnet effecting a concentrator magnetic field to attract and retain one of said first population of magnetically responsive particles and a third population of at least some other magnetically responsive particles in said second portion of said container.

10. The apparatus of claim 9 further including at least a second concentrator magnet effecting a second concentrator magnetic field to attract and retain a portion of said second population of magnetically responsive particles.

11. The apparatus of claim 9 wherein said container is a vertically oriented column and said first portion is a top of said column and said second portion is a bottom of said column.

12. The apparatus of claim 11 wherein said first and second portions of said column are separable.

13. The apparatus of claim 9 wherein at least one of said control magnet and said concentrator magnet is a permanent magnet.

14. The apparatus of claim 9 wherein at least one of said control magnet and said concentrator magnet is an electromagnet.

15. The apparatus of claim 9 wherein said controllable magnetic field is a controllable electromagnetic field provided by a controllable electromagnetic coil.

16. A method of separating at least one homogeneous population of magnetically responsive bead aggregations from a non-homogeneous population of magnetically responsive beads including said at least one homogeneous population of magnetically responsive bead aggregations and other magnetically responsive beads admixed in a fluid in a container having a first portion and a second portion, said method comprising the steps of:

controlling said non-homogeneous population of magnetically responsive beads admixed in said fluid using a control magnetic field to retain said non-homogeneous population of magnetically responsive beads in said first portion of said container;

removing said control magnetic field;

generating an electromagnetic impulse to excite and disperse said non-homogeneous population of magnetically responsive beads admixed in said fluid to effect an initial separation of said non-homogeneous population of magnetically responsive beads and to effect a first rate of motion of said at least one homogeneous population of magnetically responsive beads and at least a second rate of motion of said other magnetically responsive beads, in a first direction away from said first portion of said container and toward said second portion of said container, and applying a magnetic field to said non-homogeneous population of magnetically responsive beads co-linear with said first direction to effect a third rate of motion of said other magnetically responsive beads and a fourth rate of motion of said at least one homogeneous population of magnetically responsive bead aggregations.

17. The method of claim 16 further including the step of concentrating said at least one homogeneous population of magnetically responsive bead aggregations at a first concentrator magnet.

\* \* \* \* \*